Figure 1:
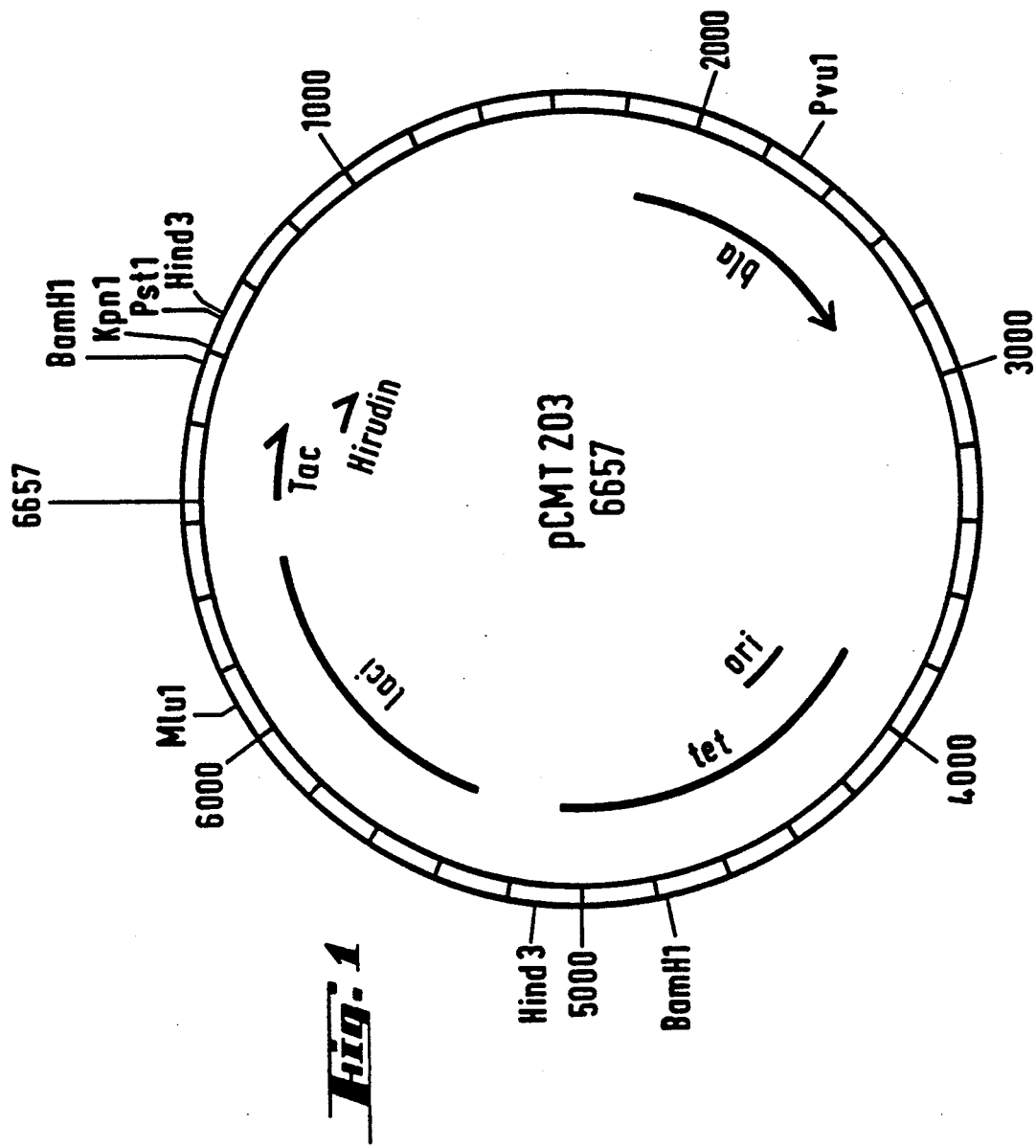

United States Patent [19]

Crause et al.

[11] Patent Number: 5,286,714
[45] Date of Patent: Feb. 15, 1994

[54] SYNTHETIC ISOHIRUDINS WITH IMPROVED STABILITY

[75] Inventors: Peter Crause, Offenbach am Main; Paul Habermann, Eppstein am Taunus; Dominique Tripier, Eppstein am Taunus; Wolfgang Ulmer, Eppstein am Taunus; Gerhard Schmid, Müchen, all of Fed. Rep. of Germany

[73] Assignee: Hoechst Aktiengesellschaft, Frankfurt am Main, Fed. Rep. of Germany

[21] Appl. No.: 985,110

[22] Filed: Dec. 3, 1992

[30] Foreign Application Priority Data

Dec. 7, 1991 [DE] Fed. Rep. of Germany ... 41 40 381.9

[51] Int. Cl.$^5$ .................. C07K 7/10; A61K 37/64
[52] U.S. Cl. .................... 514/12; 530/326; 530/416; 530/418; 536/23.5; 435/320.1; 435/69.1
[58] Field of Search .................. 530/326; 514/12; 536/23.5

[56] References Cited

U.S. PATENT DOCUMENTS

| | | | |
|---|---|---|---|
| 4,668,662 | 5/1987 | Tripier | 514/12 |
| 4,767,742 | 8/1988 | Dodt et al. | 514/12 |
| 4,791,100 | 12/1988 | Kramer et al. | 514/12 |
| 5,095,092 | 3/1992 | Badziong et al. | 530/324 |

FOREIGN PATENT DOCUMENTS

| | | |
|---|---|---|
| 41364/85 | 10/1985 | Australia . |
| 43655/85 | 12/1985 | Australia . |
| 45977/85 | 2/1986 | Australia . |
| 57787/86 | 11/1986 | Australia . |
| 60233/86 | 1/1987 | Australia . |
| 65693/86 | 6/1987 | Australia . |
| 18284/88 | 8/1989 | Australia . |
| 73680/91 | 10/1991 | Australia . |
| 1239606 | 7/1988 | Canada . |
| 0142860B1 | 5/1985 | European Pat. Off. . |
| 0158564B1 | 10/1985 | European Pat. Off. . |
| 0158986A2 | 10/1985 | European Pat. Off. . |
| 0168342B1 | 1/1986 | European Pat. Off. . |
| 0171024B1 | 2/1986 | European Pat. Off. . |
| 0193175A2 | 9/1986 | European Pat. Off. . |
| 0200655A1 | 11/1986 | European Pat. Off. . |
| 0207956B1 | 1/1987 | European Pat. Off. . |
| 0209061A3 | 1/1987 | European Pat. Off. . |
| 0227938B1 | 7/1987 | European Pat. Off. . |
| 0316650A3 | 5/1989 | European Pat. Off. . |
| 0324712A3 | 7/1989 | European Pat. Off. . |
| 0364942A2 | 4/1990 | European Pat. Off. . |
| 0448093A3 | 9/1991 | European Pat. Off. . |
| WO85/04418 | 10/1985 | PCT Int'l Appl. . |

OTHER PUBLICATIONS

Harvey et al., "Cloning & Expression of a cDNA Coding for the Anti-Coagulant Hirudin from the Blood Sucking Leech, Hirudo Medicinalis," PNAS 83: 1084–1088 (1986).

Baskova et al., "Hirudin from Leech Heads and Whole Leeches and Pseudo-Hirudin from Leech Bodies," Thrombosis Research 30:459–467 (1983).

Bowie et al., "Deciphering the Message in Protein Sequences: Tolerance to Amino Acid Substitutions," Science 247 1306–1310 (1990).

Smith et al., Principles of Biochemistry: General Aspects, 7th Ed., pp. 32–33, pp. 814–815.

(List continued on next page.)

Primary Examiner—Robert A. Wax
Assistant Examiner—Rebecca Prouty
Attorney, Agent, or Firm—Finnegan, Henderson, Farabow, Garrett & Dunner

[57] ABSTRACT

The invention relates to novel synthetic isohirudins which have improved stability owing to exchange in the region of the Asp-Gly motif. This results, on the one hand, in an increase in the yield during workup and, on the other hand, in making possible pharmaceutical formulation as directly injectable solution ready for use.

9 Claims, 4 Drawing Sheets

OTHER PUBLICATIONS

Dodt et al., "Interaction of Site Specific Hirudin Variants with δ-thrombin," FEBS Letters, vol. 229 (1): 87–90 (1988).

Dodt et al., "The Complete Amino Acid Sequence of Hirudin, a Thrombin Specific Inhibitor. Application of Colour Carboxymethylations", FEBS Letters, vol. 164 (2): pp. 180–184 (1984).

Geiger et al., "Deamidation, Isomerization, and Racemization at Asparaginyl and Aspartyl Residues in Peptides," The Journal of Biological Chemistry, vol. 262, No. 2, 1987, pp. 785–794.

Stephenson et al., "Succinimide Formation from Aspartyl and Asparaginyl Peptides as a Model for the Spontaneous Degradation of Proteins," The Journal of Biological Chemistry, vol. 264, No. 11, 1989, pp. 6164–6170.

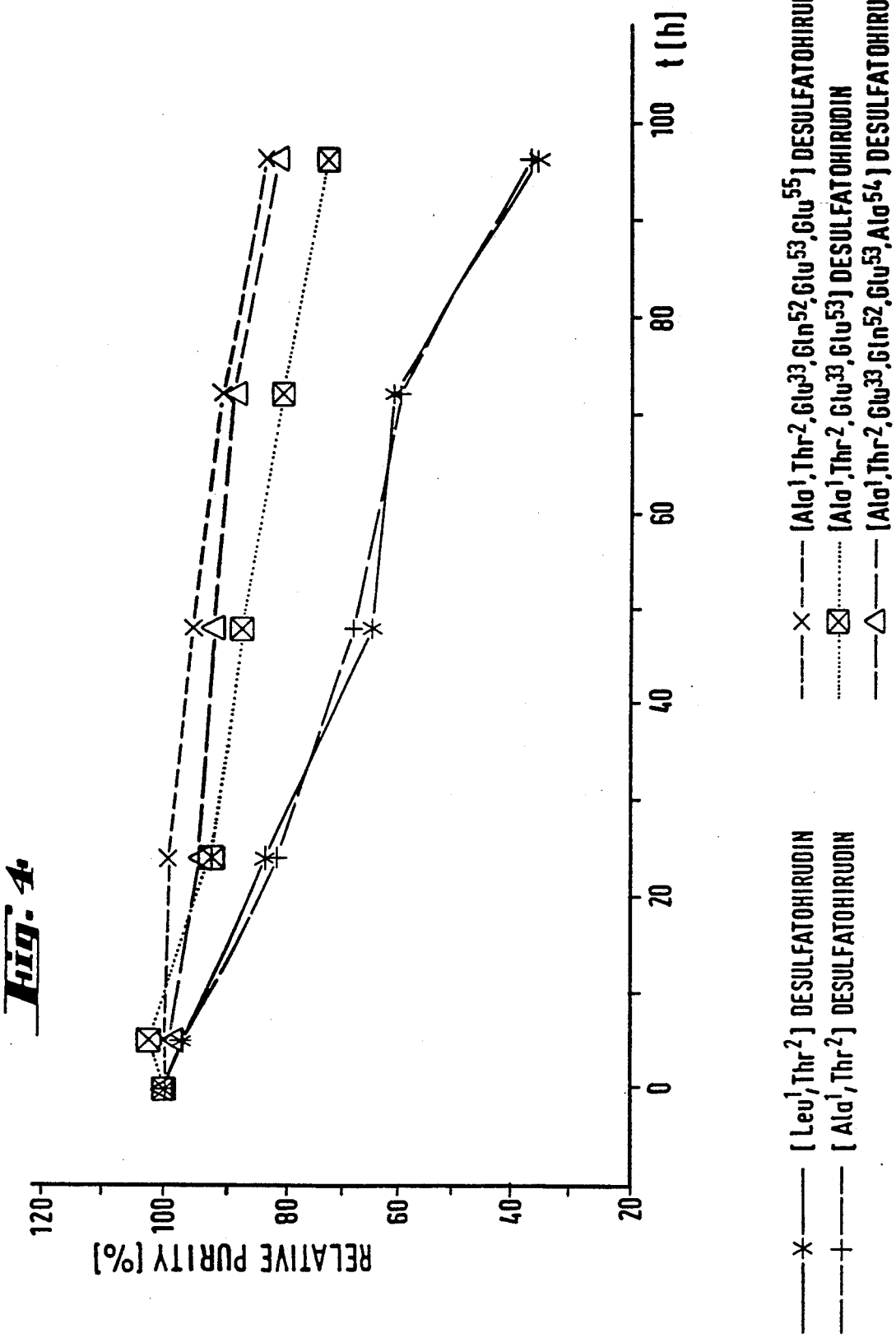

SYNTHETIC ISOHIRUDINS WITH IMPROVED STABILITY

The invention relates to novel synthetic isohirudins which have improved stability owing to exchange in the region of the Asp-Gly motif. This results, on the one hand, in an increase in the yield during workup and, on the other hand, in making possible pharmaceutical formulation as directly injectable solution ready for use.

High-affinity thrombin inhibitors of medical value, whose use in human medicine is expected to lead to considerable advances in thrombosis therapy, from the leech Hirudo medicinalis are known. These peptide-like inhibitors are called hirudins, and a large number of natural isohirudins which differ in only a few amino acids in the sequence is known. Natural isohirudins are described, for example, in EP-A 142 860, EP-A 158 564, EP-A 158 986, EP-A 168 342, EP-A 171 024, EP-A 193 175, EP-A 200 655, EP-A 209 061, EP-A 227 938. The development of recombinant DNA technology in the last decade has now made it possible to make hirudins available on an industrial scale by using microorganisms modified by genetic manipulation. Processes for the preparation of isohirudins based on natural sequences are described, for example, in EP-A 171 024 and EP-A 200 655 and the literature cited therein.

However, the requirements to be met by a drug nowadays goes far beyond the therapeutic activity. These include economy of manufacture, clinical convenience and high stability in view of a long duration of use.

In order for an improved therapy to be able to benefit a large number of patients, including from economic points of view, it is necessary to keep the costs of manufacturing the drug low. In the case of genetically engineered products, this can be aimed at by developing optimized expression systems but also by adapting the drug to a system of this type. Isohirudins structurally optimized in this respect are described, for example, in EP-A 324 712 and EP-A 448 093.

The aspect of duration of use ought to be taken into account by a high stability of the drug, so that therapeutic and pharmacological complications based on the formation of breakdown products are prevented. The isohirudins known from the leech, as well as desulfatohirudins from microorganisms modified by genetic manipulation are unsatisfactory in this respect because they are prone, owing to their structure, to form byproducts by internal chemical transformation. Also from the aspect of economy of the workup process the a priori prevention of the formation of byproducts is advantageous, since removal thereof is dispensed with. This results in improved yields.

An improved stability would additionally make possible a formulation which permits storage and use of the drug with minimal expense. In the case of hirudin, a stable, directly injectable solution ready for use represents a formulation of this type, which additionally ought to be distinguished by long-term utilizability. In this connection, the chemical instability of the known isohirudins is, in fact, a limiting factor because the temperature-dependent formation of byproducts by the dissolved substance even on storage in a refrigerator permits only a limited (short) duration of use of a formulation of this type, and economy can be attained only with difficulty.

Figure 2:
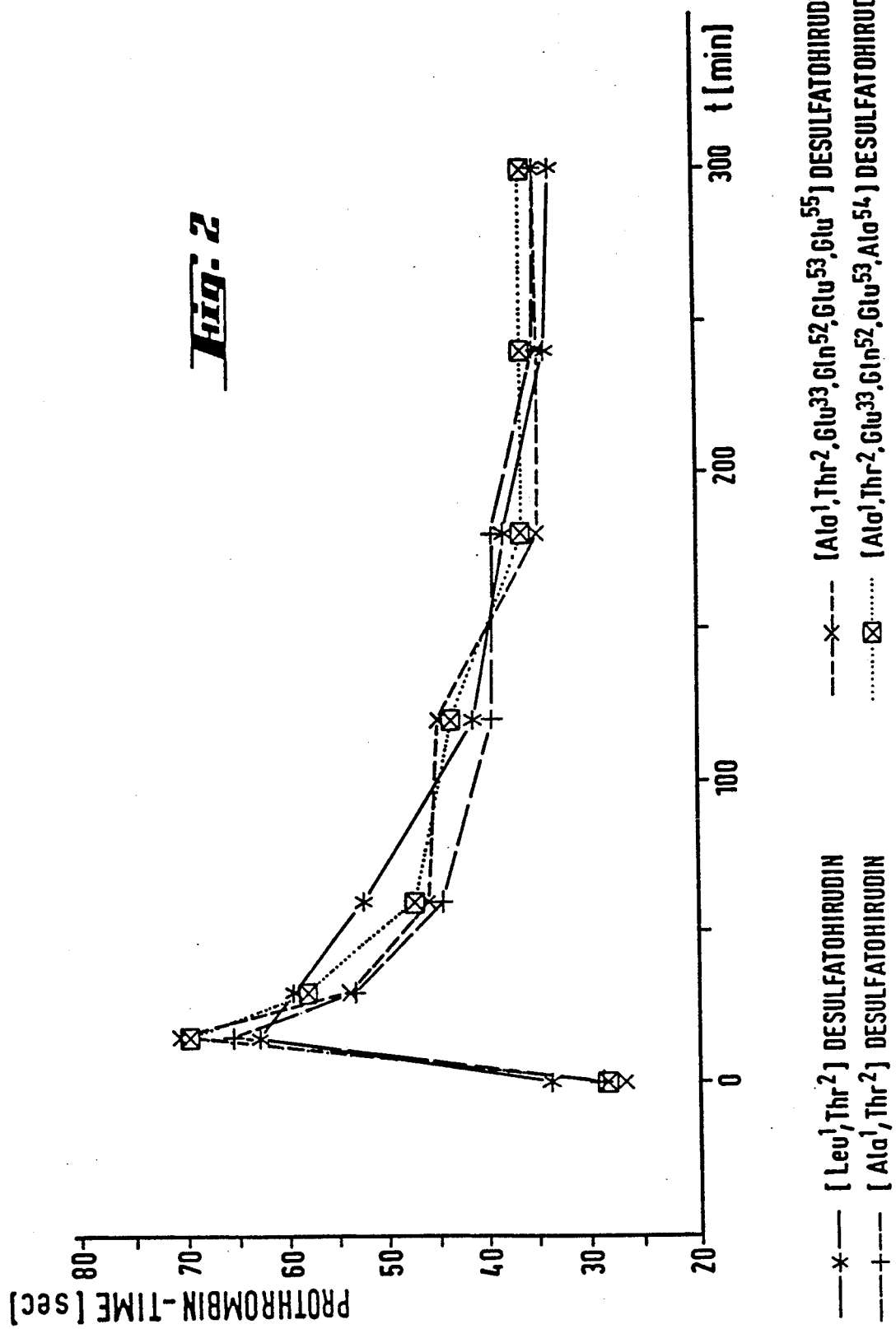

The known natural isohirudins and desulfatohirudins derived therefrom for pharmaceutical development differ in only a few amino-acid units, and it is possible to distinguish variable and conservative regions in the sequence. The conservative regions include the sequences -Ser$^{32}$-Asp(Asn)$^{33}$-Gly$^{34}$- and -Asn$^{52}$-Asp(Asn)$^{53}$-Gly$^{54}$-Asp$^{55}$-. The numbering is that of the sequence with 65 amino acids published by Dodt et al., FEBS LETTERS 165 (1984) 180–183. Protein chemical analyses of hirudin breakdown products have now shown that these sequence motifs are predominantly responsible for the chemical instability of hirudin. Deamidation of asparagine to aspartic acid need not be taken into account in this context, because it leads to another natural isohirudin structure. Essential for hirudin breakdown is isomerization and racemization at the two -Asp-Gly- sequences. The significance of these reactions for the breakdown of proteins is known from the literature (JBC 262, 1987, pages 785–793 and JBC 264, 1989, pages 6164–6170). The significance of the carboxy-terminal structure of hirudin for the high-affinity binding to thrombin is likewise known. Amino-acid exchange in regions which have sequences conservative in nature and which are involved in the binding is associated with the risk of loss of affinity. Surprising, it has now been found that certain stability-improving modifications in conservative regions can be carried out without impairing the affinity for thrombin and thus the activity (Example 7, Tab. 1 and Example 8, FIG. 2).

It has additionally emerged, surprisingly, that, despite the exchanges which have been carried out, even with more than one amino acid, no increase in the antigenicity occurs.

It has furthermore been found that both -Asp-Gly- sequences contribute equally to the instability of hirudin. It is possible substantially to reduce byproduct formation only by modification of both sequence regions (Example 9, Table 2). The time course of byproduct formation by the parent compounds and by the optimized desulfatohirudins both at acidic (Example 11, FIG. 3) and at physiological pH (Example 10, FIG. 4) shows that the amino terminus has no effect on the stability, and a modification thus does not contribute to stabilization. It follows from this that the optimizations shown for the example [Ala$^1$,Thr$^2$] desulfatohirudin are applicable to isohirudins with different amino terminus (for example [Val$^1$,Val$^2$]- and [Ile$^1$,Thr$^2$]-desulfatohirudin).

Detailed analysis of the stability of various synthetic isohirudins (FIG. 3 and 4) discloses, however, for the example of [Ala$^1$,Thr$^2$,Glu$^{33}$,Glu$^{53}$] desulfatohirudin (Seq ID No. 23) that simple exchange of the aspartic acid does not have the optimal effect. The superior stability of [Ala$^1$,Thr$^2$,Glu$^{33}$,Gln$^{52}$,Glu$^{53}$,Ala$^{54}$]-desulfatohirudin (Seq ID No. 1) and [Ala$^1$,Thr$^2$,Glu$^{33}$,Gln$^{52}$,Glu$^{53}$Glu$^{55}$]-desulfatohirudin (Seq ID No. 2) surprisingly shows that the additional exchange of asparagine with glutamine at position 52 makes an essential contribution to the stabilization.

The invention consequently relates to isohirudins with improved stability, wherein there is Glu at position 33, Gln, Glu, Asn or Asp at position 52, Glu at position 53, Gly or Ala at position 54 and Glu or Asp at position 55 (Seq ID No. 3).

Preferred compounds have the formula I

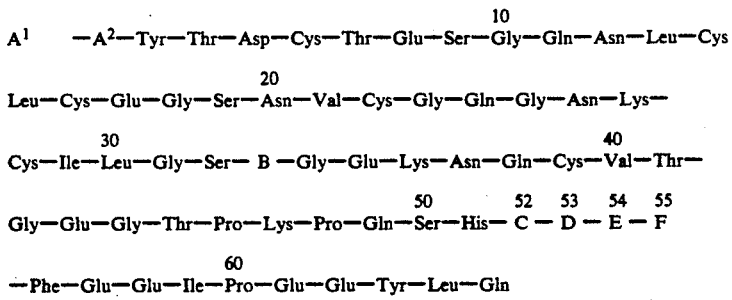

where
- $A^1$ is Leu, Ala, Ile or Val,
- $A^2$ is Thr or Val,
- B is Glu,
- C is Gln or Glu,
- D is Glu,
- E is Gly or Ala, and
- F is Asp or Glu (Seq ID No. 4).

Particularly preferred compounds are [Ala$^1$ or Leu$^1$, Thr$^2$, Glu$^{33}$, Gln$^{52}$-Glu$^{53}$-Ala$^{54}$-] desulfatohirudin (Seq ID No. 5) and [Ala$^1$ or Leu$^1$, -Thr$^2$, Glu$^{33}$, Gln$^{52}$-Glu$^{53}$, Glu$^{55}$-] desulfatohirudin (Seq ID No. 6).

The synthetic hirudin derivatives according to the invention can be produced by microorganisms or else by chemical synthesis. Production in baker's yeast or *E. coli* is preferred.

The chemical stability of optimized isohirudins in conjunction with a highly efficient expression system allows the workup processes to be relatively simple and thus low-cost. In this connection, combination of biochemical methods known per se may lead to processes which may differ slightly from one another. The invention likewise relates to process variants of this type. Derivatives of [Ala$^1$,Thr$^2$] desulfatohirudin may, for example, be produced in an expression system disclosed in European Patent Application EP-A 448 093, in which case the workup comprises only a few steps: the cell suspension at the end of the fermentation or a cell-free culture filtrate is acidified to pH 2–4 (for example with formic acid, HCl), and a protein-containing precipitate produced thereby can be removed by centrifugation or filtration. The product can, in the simplest case, where this is permitted by the culture medium used, be highly concentrated from the clear supernatant by reversed phase chromatography. On the other hand, when complex media are used, it is advantageous to reduce the salt content of the solution, for example by ultra/diafiltration, in order then to carry out an ion exchange chromatography on a cation exchanger, for example Fractogel® EMD-SO$_3^-$. In place of the ultrafiltration, it is also possible to carry out a hydrophobic adsorption onto a suitable resin as described, for example, in European Patent Application EP-A 316 650. The product from the cation exchange chromatography can then be introduced directly into the reversed phase chromatography (for example on Lichroprep® RP18) which yields a high-purity product. It is possible if necessary to remove remaining impurities by an additional anion exchange chromatography, for example on Q-Sepharose. Yields >50% can be achieved by appropriate optimization of the individual stages.

When an expression system disclosed in European Patent Application EP-A 316 650 is used to prepare stabilized derivatives of [Leu$^1$,Thr$^2$]-desulfatohirudin, the workup can be carried out analogously, but it is advisable in this case to further concentrate the product before the cation exchange chromatography by a batch anion exchanger step as described, for example, in European Patent Application EP-A 316 650.

EXAMPLE 1

Construction of the Vector pCMT203

Biotechnological operations such as setting up seed cell banks or fermentation of a strain are preferably carried out under selection pressure on the host/vector system employed. This minimizes the risk of contamination by foreign microorganisms. In compliance with the guidelines of the American Health Authority, the antibiotic ampicillin should not be used in processes for producing recombinant proteins.

The plasmids pCM7051 and pCM7053 have been described in European Patent Application EP-A 448 093. Improvement of the plasmids in the aspect described above can be achieved by extending the vector DNA by the known resistance to tetracycline.

To do this, DNA of the plasmid pCM7051 is linearized with NruI and ligated to the isolated 1.1 kb NruI fragment from the plasmid pCM7053. This DNA fragment contains the 5'-terminal part of the tetracycline-resistance gene which is missing from the plasmid pCM7051. Competent cells of the *E. coli* strain Mc1061 are transformed with the ligation mixture and plated out on NA agar plates which contain 12.5 mg/l tetracycline. Transformants are obtained after incubation at 37° C. overnight. Plasmid DNA is reisolated therefrom and characterized by restriction analysis. The DNA of a correct plasmid is subsequently reacted with the enzymes AvaI and NdeI in accordance with the manufacturers' instructions and fractionated by gel electrophoresis. The larger of the two fragments is isolated and the protruding ends are filled in with Klenow polymerase. Subsequently, the fragment is autoligated and again transformed into *E. coli* Mc1061. After characterization of the DNA by restriction analysis, the required plasmids are called pCMT203 (FIG. 1).

EXAMPLE 2

Construction of Hirudin Variants with Alanine as N-terminal Amino Acid

Hirudin variants which start with alanine are to be expressed in *E. coli*. Used for the cloning were the vectors pCM7053 and pcmT203 described in Example 1 and the plasmid of FIG. 3, which is described in EP-A 171 024, with the synthetic DNA sequence for hirudin, which is called DNA sequence I. This plasmid is called plasmid pK152 hereinafter. In addition, the following oligonucleotides were synthesized using the "391 DNA synthesizer" DNA synthesizing machine supplied by Applied Biosystems:

| | | |
|---|---|---|
| Hir1 | 5'-CCCGAAACCGCAGTCTCACCAGGAAGGCGAATT-3' | (Seq ID No. 7) |
| Hir2 | 5'-CGAATTCGCCTTCCTGGTGAGACTGCGGTTTCGGGGTAC-3' | (Seq ID No. 8) |
| Hir5 | 5'-GATCCGAAGGTGAAAAGAACCAGTGCGTTACTGGCGAAGGTAC-3' | (Seq ID No. 9) |
| Hir6 | 5'-CTTCGCCAGTAACGCACTGGTTCTTTTCACCTTCG-3' | (Seq ID No. 10) |
| Hir13 | 5'-CCCGAAACCGCAGTCTCATAACGAGGGCGACTT-3' | (Seq ID No. 11) |
| Hir14 | 5'-CGAAGTCGCCCTCGTTATGAGACTGCGGTTTCGGGGTAC-3' | (Seq ID No. 12) |
| Hir15 | 5'-CCCGAAACCGCAGTCTCATCAGGAGGCTGACTT-3' | (Seq ID No. 12) |
| Hir16 | 5'-CGAAGTCAGCCTCCTGATGAGACTGCGGTTTCGGGGTAC-3' | (Seq ID No. 13) |

EXAMPLE 2a

Construction of Hirudin Variant 13 (Ala$^1$,Glu$^{33}$,Glu$^{52}$,Glu$^{53}$,Glu$^{55}$)(Seq ID No. 15) in plasmLd pSCH13

DNA of the plasmid pK152 is reacted with the enzymes BamHI and KpnI and the two resulting fragments are separated from one another by gel electrophoresis. The large fragment is isolated and reacted in a T4 DNA ligase reaction with the oligonucleotide sequences Hir5 and Hir6 previously hybridized to the double strand. Competent E. coli Mc1061 cells are transformed with the ligation mixture. In parallel with this, the pK153 vector fragment is ligated to itself in an autoligation reaction and likewise transformed. The transformation mixtures are plated out on NA plates which contain 20 mg/l ampicillin and incubated at 37° C. overnight. The experiment is evaluated the next morning. The cloning is regarded as promising when the ligation to the oligonucleotide fragment yields at least 100 times more transformants than the autoligation. Plasmid DNA is then isolated from transformants from the cloning reaction and is characterized by restriction analysis. The BamHI/HindIII fragment which contains the hirudin peptide sequence 32-65 with Asp$^{55}$ exchanged by Glu$^{55}$ is isolated from plasmid DNA which shows the correct restriction pattern. This fragment is ligated to the vector pCM7053 opened with BamHI/HindIII. The result is the plasmid pCM7053Var3. The plasmid contains the DNA sequence for a modified hirudin which has the amino acid Glu in position 55. DNA from the plasmid pK152 is cleaved with the restriction enzymes KpnI and BstbI. After fractionation by gel electrophoresis, the large vector fragment is isolated. This fragment is ligated to the oligonucleotides HirI and HirII previously hybridized to the double strand. In accordance with the process described above, a derivative of the plasmid pK153 is produced. This is called variant 1. The BamHI/HindIII fragment from this plasmid is isolated and ligated to the vector pCM7053 opened with BamHI/HindIII. The result is the plasmid pCM7053Var1 which codes for a modified hirudin which has the amino acids Gln, Glu and Glu in position 52, 53 and 55. The plasmid is distinguished from pCM7053 by additionally having a recognition site for the restriction enzyme EcoRI.

DNA of the plasmids pCM7053Var1 and pCM7053Var3 is subjected to double digestion with the enzymes KpnI and MluI and fractionated by gel electrophoresis. Two fragments are produced in each case, and the larger of the two is isolated in the case of the pCM6053Var1 mixture and the smaller of the two fragments is isolated in the case of pCM7053Var3. The two fragments are combined in one ligation to give the new plasmid pVar13 which is expressed in the strain E. coli Mc1061. Hirudin is isolated as in Example 5 and characterized by amino-acid analysis. The correctness of the construction of the plasmid pVar13 is confirmed by the expected amino-acid composition.

DNA of the plasmids pCMT203 and pVar13 is now reacted with the restriction enzymes MluI and PvuI and fractionated by gel electrophoresis. Two fragments are produced in each case, and the larger is isolated in each case. The fragments isolated in this way are combined in a ligase reaction to give the plasmid pSCH13. The structure thereof is confirmed by restriction enzyme analysis and DNA sequence analysis. This plasmid is introduced, by transformation in a known manner, into the E. coli K12 secretor mutants described in European Patent Application EP-A 448 093.

EXAMPLE 2b

Construction of the Hirudin Variant 83 (Ala$^1$,Glu$^{33}$,Glu$^{53}$) (Seq. ID No. 16) in plasmid pSCH83

The KpnI/BstbI pK152 vector fragment described in Example 2a is ligated to the oligonucleotides Hir13 and Hir14 previously hybridized to the double strand. A plasmid called variant 8 is produced. The BamHI/HindIII fragment from this plasmid is isolated as in Example 2a and introduced into the vector pCM7053 opened with BamHI/HindIII. The plasmid pCMVar8 is produced, and the smaller KpnI/MluI fragment of this is isolated. The latter is ligated to the large KpnI/MluI fragment from plasmid pCMVar3. The plasmid pVar83 is produced as expressed in the strain, E. coli Mc1061. After isolation of the hirudin derivative and subsequent amino-acid analysis, the plasmid structure is confirmed so that the MluI/PvuI fragment is isolated as in Example 2a and is ligated to the large MluI/PvuI vector fragment from plasmid pCMT203 to give the plasmid pSCH83. This plasmid is introduced into the secretor mutants described above.

EXAMPLE 2c

Construction of the hirudin variant 93 (Ala$^1$,Glu$^{33}$,Gln$^{52}$,Glu$^{53}$,Ala$^{54}$)(Seq. ID No. 17) in plasmid pSCH93

The plasmid pSCH93 is constructed in analogy to Example 2b. This entails, in the first cloning step, the BstbI/KpnI pK152 fragment being reacted with the oligonucleotides Hir15 and Hir16 hybridized to the double strand to give the plasmid called variant 9.

EXAMPLE 3

Expression of the plasmids pSCH13, pSCH83 and pSCH93

The plasmids pSCH13, pSCH83 and pSCH93 are expressed both in shaken flasks and on the 10-liter scale as described in European Patent Application EP-A 448 093. The described strains or variants thereof are used for this. The media, induction conditions and fermentation times for the expression of cultures on the cubic meter scale may, by their nature, be altered, which is known to the person skilled in the art.

EXAMPLE 4

Cloning and Expression of the Hirudin Variants 13 and 93 in Baker's Yeast

A synthetic hirudin which has, in a modification of the natural sequence, a N-terminal amino acid leucine is described in European Patent Application EP-A 324 712. This hirudin can likewise be further optimized when the modifications described previously for the variants 13 and 93 are carried out in the sequence following leucine, from amino acid 2. In this connection, recourse is had by way of example to the vectors and strains described in this Application. The person skilled in the art is aware that every other yeast expression system which results in secretion of hirudin or variants thereof can also be used.

The cloning vector 7 described in European Patent Application EP-A 324 712 is opened with BamHI and HindIII and in each case ligated to the BamHI/HindIII fragment which has been isolated from the plasmid pSCH13 or pSCH93 and which comprises amino acids of the carboxyl-terminal part of the hirudin sequence which are missing from the cloning vector in each case. The plasmids p713 and p793 are produced and are characterized by restriction analysis. Subsequently, the EcoRI/HindIII fragment is isolated from correct DNA of these plasmids, and the protruding ends are filled in a Klenow polymerase reaction. The fragments prepared in this way are ligated in each case to the blunt-ended vector fragment from the plasmid yEP13 as described in Example 1 of European Patent Application EP-A 324 712. The plasmids pHABVar131 and pHABVar132 which differ only with regard to the orientation of the inserted fragment and which code for a hirudin derivative which has the amino acids Leu$^1$, Glu$^{33}$, Gln$^{52}$, Glu$^{53}$ and Glu$^{55}$, and the plasmids pHABVar931 and pHABVar932 which likewise differ only in the orientation of the inserted fragment and which code for a hirudin derivative which has the amino acids Leu$^1$, Glu$^{33}$, Gln$^{52}$, Glu$^{53}$ and Ala$^{54}$ are produced. The plasmids are, by way of example, transformed into the yeast strains described in the Application. Expression and purification of the hirudin derivatives can be carried out by the procedure described therein. It is known that it is possible in the purification to dispense with centrifugation and subsequent adsorption chromatography when, for example, the Millipore Pellicon ultrafiltration system is used. The methods used here are described for the laboratory scale. For cultures on the cubic meter scale, other fermentation times, culture conditions and steps in the workup may be necessary. This is known to the person skilled in the art.

EXAMPLE 5

Purification of [Ala$^1$,Thr$^2$,Glu$^{33}$,Gln$^{52}$,Glu$^{53}$,Glu$^{55}$]-Desulfatohirudin (Seq. ID No. 2)

A cell-free culture supernatant with 3.6 g of hirudin per 1 was adjusted to pH 3 by addition of formic acid. The precipitate resulting after 1 h at RT was spun down in a CEPA centrifuge. The conductivity of the clear supernatant was reduced to <2.5 mS/cm by diafiltration. The product was then prepared with high purity by consecutive chromatography steps on Fractogel ® EMD-SO$_3^-$, Lichroprep ® RP18 and Q-Sepharose.

Remaining salts and buffer constituents were removed from the Q-Sepharose eluate by combined ultra/diafiltration, after which it was possible to obtain the product as dry substance by lyophilization.

EXAMPLE 6

Purification of [Ala$^1$,Thr$^2$,Glu$^{33}$,Gln$^{52}$,Glu$^{53}$,Ala$^{54}$]-Desulfatohirudin (Seq. ID No. 1)

At the end of the fermentation, the culture solution was acidified to pH 3 in the presence of the cellular matter. Biomass and resulting precipitate were removed in a separator. 5% w/v Diaion HP20 were added to the clear supernatant, resulting in quantitative adsorption of the hirudin. After removal of the mother liquor by filtration, the resin was washed once with water. The product was then desorbed with 30% strength isopropanol acidified to pH 3. The clear eluate was further processed as in Example 5, starting with the cation exchange chromatography, and then a highly pure dry product was obtained after lyophilization.

EXAMPLE 7

Comparative K Value Determination On Optimized Isohirudins

K$_i$ values were determined by the method of Stone and Hofsteenge (Biochemistry 25, pages 4622–4628, 1986): 0.2 ml of a 1.25 mM solution of D-HHT-Gly-Arg-pNA was equilibrated at 25° C. with 1.7 ml of 0.1M tris, 0.2M NaCl and 0.1% (v/v) Triton X-100 pH 8.3 and 0.1 ml of the isohirudin to be tested in 145 mM NaCl. Binding was started by adding 0.05 ml of thrombin solution. The absorption at 405 nm was recorded for a period of 10–20 min.

The reaction follows the equation:

$$[P] = v_s^* + )v_o - v_s)(l - e^{-k^* t})/k + d,$$

where

[P] = product concentration (nitroaniline)
V$_o$ = initial rate
v$_s$ = reaction rate in the equilibrium state
d = [P] at t = 0

The rate constant k was determined by non-linear regression. Extrapolation of k at various inhibitor concentrations to [1] = 0 according to $$k = k_{on}^*[1]/(1 + S/K_m) + k_{off}$$

yields the rate constants k$_{on}$ and k$_{off}$ and thus K$_i$ = k$_{off}$/k$_{on}$.

TABLE 1

K$_i$ values of optimized desulfatohirudins

| Compound | K$_{i(app.)}$ [M] |
|---|---|
| [Ile$^1$, Thr$^2$] desulfatohirudin$^1$ | 6.1 × 10$^{-10}$ |
| [Leu$^1$, Thr$^2$] desulfatohirudin$^2$ | 1.4 × 10$^{-10}$ |
| [Ala$^1$, Thr$^2$] desulfatohirudin$^3$ | 2.0 × 10$^{-10}$ |
| [Ala$^1$, Thr$^2$, Glu$^{33}$] desulfatohirudin | 1.6 × 10$^{-10}$ |
| | (Seq. ID No. 18) |
| [Ala$^1$, Thr$^2$, Gln$^{52}$, Glu$^{53}$, Glu$^{55}$] desulfatohirudin | 1.9 × 10$^{-10}$ |
| | (Seq. ID No. 19) |
| [Ala$^1$, Thr$^2$, Glu$^{33}$, Gln$^{52}$, Glu$^{53}$, Glu$^{55}$] desulfatohirudin | 3.0 × 10$^{-10}$ |
| | (Seq. ID No. 2) |
| [Ala$^1$, Thr$^2$, Ala$^{54}$] desulfatohirudin | 2.7 × 10$^{-10}$ |
| | (Seq. ID No. 20) |
| [Ala$^1$, Thr$^2$, Glu$^{33}$, Ala$^{54}$] desulfatohirudin | 3.5 × 10$^{-10}$ |
| | (Seq. ID No. 21) |
| [Ala$^1$, Thr$^2$, Glu$^{53}$] desulfatohirudin | 3.8 × 10$^{-10}$ |
| | (Seq. ID No. 22) |
| [Ala$^1$, Thr$^2$, Glu$^{33}$, Glu$^{53}$] desulfatohirudin | 3.7 × 10$^{-10}$ |
| | (Seq. ID No. 23) |
| [Ala$^1$, Thr$^2$, Gln$^{52}$, Glu$^{53}$, Ala$^{54}$] desulfato- | 2.2 × 10$^{-10}$ |

TABLE 1-continued

| K_i values of optimized desulfatohirudins | |
|---|---|
| Compound | $K_{i(app.)}$ [M] |
| hirudin | (Seq. ID No. 24) |
| [Ala¹, Thr², Glu³³, Gln⁵², Glu⁵³, Ala⁵⁴] desulfatohirudin | $3.1 \times 10^{-10}$ (Seq. ID No. 1) |

¹Desulfatohirudin derived from a natural isohirudin.
²Optimized desulfatohirudin for yeast expression according to EP-A 324 712.
³Optimized desulfatohirudin for E. coli secretion expression according to EP-A 448 093.

EXAMPLE 8

Effect of Optimized [Ala¹,Thr²] Desulfatohirudin Analogs on the Partial Thromboplastin Time (PTT) in Rhesus Monkeys [Leu¹,Thr²] desulfatohirudin, [Ala¹,Thr²] desulfatohirudin, [Ala¹,Thr²,Glu³³,Gln⁵²,Glu⁵³,Glu⁵⁵] desulfatohirudin (Seq. ID No. 2) and [Ala¹,Thr²,Glu³³,Gln⁵²,Glu⁵³,Ala⁵⁴] desulfatohirudin (Seq. ID No. 1) were administered intravenously in a dose of 0.5 mg/kg to male rhesus monkeys with a body weight of 6.5±1.6 kg. Blood samples were then taken at defined intervals for determination of coagulation parameters. The partial thromboplastin time (PTT) was determined as follows (FIG. 2): 0.1 ml of citrated plasma and 0.1 ml of PTT reagent from human platelets (Behringwerke) were mixed in a test tube preheated to 37° C. and maintained at 37° C. for exactly 2 min for complete activation of the intrinsic coagulation system. Subsequently, 0.1 ml of 0.025M calcium chloride solution was added, and the coagulation was measured in a coagulometer (according to Schnitger and Gross).

EXAMPLE 9

20-hour stability of [Ala¹,Thr²] desulfatohirudin analogs at pH 7 and 60° C.

The compound to be tested was dissolved in 0.5 mg/ml in 20 mM NaP, pH 7, 300 mM NaCl and incubated at 60° C. for 20 h. Samples were taken at times t=0 and t=20 h and analyzed by RP HPLC (Nucleosil®) and anionic exchange chromatography (Mono Q®). The content of newly formed byproducts was calculated.

TABLE 2

| Stability of optimized desulfatohirudins under stress conditions: 20 h, 60° C., pH 7 | |
|---|---|
| Compound | % newly formed byproducts |
| [Ala¹, Thr²] desulfatohirudin¹ | 23.0 |
| [Ala¹, Thr², Glu³³] desulfatohirudin | 15.2 (Seq. ID No. 18) |
| [Ala¹, Thr², Gln⁵², Glu⁵³, Glu⁵⁵] desulfatohirudin | 14.6 (Seq. ID No. 19) |
| [Ala¹, Thr², Glu³³, Gln⁵², Glu⁵³, Glu⁵⁵] desulfatohirudin | 3.2 (Seq. ID No. 2) |

¹Parent compound

EXAMPLE 10

Stability of [Ala¹,Thr²] Desulfatohirudin Analogs at pH 6.5 and 60° C.

The purified isohirudins, as lyophilisate, were dissolved at 1 mg/ml in water and adjusted to pH 6.5 with 1M Na₂HPO₄. After sterilization by filtration, the solutions were incubated at 60° C. in a shaking water bath with exclusion of light. Samples were taken at times t=0, 5, 24, 48, 72 and 96 h and analyzed by RP HPLC (Nucleosil®) and ion exchange chromatography (Mono Q®) for the content of byproducts therein. The purity at time t=x is shown relative to the purity at t=0, with in each case the less favorable value from the two analysis systems being used as bases (FIG. 4).

EXAMPLE 11

Stability of [Ala¹,Thr²] Desulfatohirudin Analogs at pH 4 and 60° C.

Figure 3:
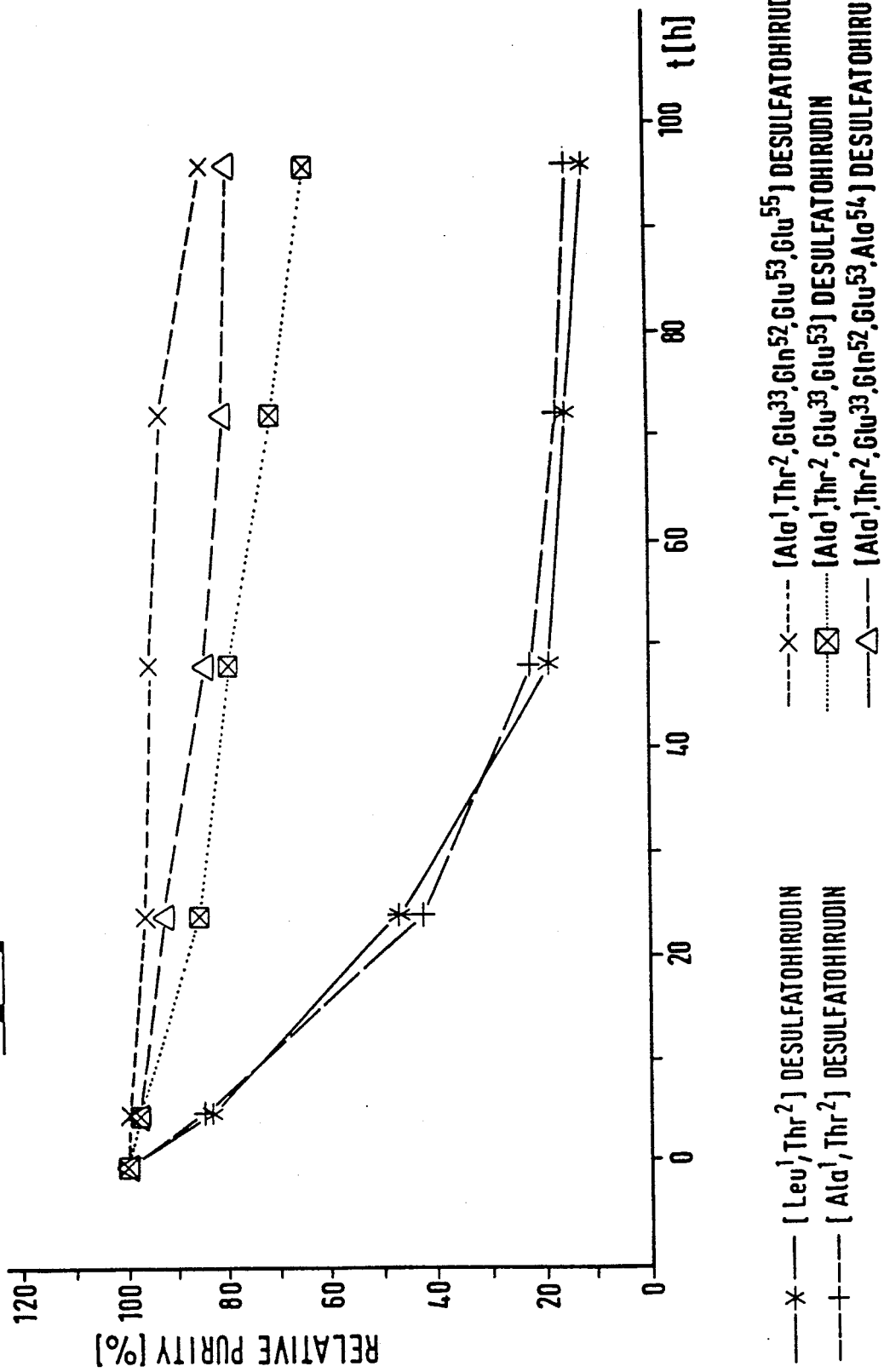

The purified isohirudins, as lyophilisate, were dissolved at 1 mg/ml in water and adjusted to pH 4 with 1M acetic acid. Incubation and analyses were carried out as in Example 10 (FIG. 3).

---

We claim:

1. An isohirudin with the following amino acids
Glu at position 33
Gln, Glu, Asn or Asp at position 52
Glu at position 53
Gly or Ala at position 54
Asp or Glu at position 55 (Seq. ID No. 3).

2. An isohirudin as claimed in claim 1 with the formula

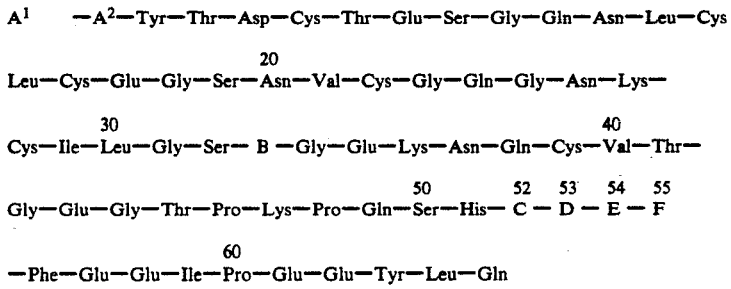

where
A¹ is Leu, Ala, Ile or Val,
A² is Thr or Val,
B is Glu,
C is Gln or Glu,
D is Glu,
E is Gly or Ala, and
F is Asp or Glu (Seq. ID No. 4).

3. An isohirudin as claimed in claim 1, where position 1 denotes Ala or Leu, Thr is at position 2, Glu is at position 33, Gln is at position 52, Glu is at position 53, Gly is at position 54 and Glu is at position 55 (Seq. ID No. 25).

4. An isohirudin as claimed in claim 2, where position 1 denotes Ala or Leu, Thr is at position 2, Glu is at position 33, Gln is at position 52, Glu is at position 53, Gly is at position 54 and Glu is at position 55 (Seq. ID No. 26).

5. An isohirudin as claimed in claim 1, wherein position 1 denotes Ala or Leu, Glu is at position 33, Gln is at position 52, Glu is at position 53, Ala is at position 54 and Asp is at position 55 (Seq. ID No. 27).

6. A pharmaceutical which contains one or more isohirudins as claimed in claim 1 as active ingredient.

7. A pharmaceutical which contains one or more isohirudins as claimed in claim 2 as active ingredient.

8. A pharmaceutical formulation of an isohirudin as claimed in claim 1, wherein the active substance is present in a concentration of 1–500 mg/ml and at a pH between 4 and 8 in dissolved form for parenteral (i.v. and s.c.) administration.

9. A pharmaceutical formulation of an isohirudin as claimed in claim 2, wherein the active substance is present in a concentration of 1–500 mg/ml and at a pH between 4 and 8 in dissolved form for parenteral (i.v. and s.c.) administration.

* * * * *

SEQUENCE LISTING ( 1 ) GENERAL INFORMATION:

( i i i ) NUMBER OF SEQUENCES: 27

( 2 ) INFORMATION FOR SEQ ID NO:1:

( i ) SEQUENCE CHARACTERISTICS:
        ( A ) LENGTH: 65 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

```
Ala Thr Tyr Thr Asp Cys Thr Glu Ser Gly Gln Asn Leu Cys Leu Cys
 1               5                  10                      15

Glu Gly Ser Asn Val Cys Gly Gln Gly Asn Lys Cys Ile Leu Gly Ser
             20                  25                  30

Glu Gly Glu Lys Asn Gln Cys Val Thr Gly Glu Gly Thr Pro Lys Pro
         35                  40                  45

Gln Ser His Gln Glu Ala Asp Phe Glu Glu Ile Pro Glu Glu Tyr Leu
         50                  55                      60

Gln
```

65

(2) INFORMATION FOR SEQ ID NO:2:

(i) SEQUENCE CHARACTERISTICS:
  (A) LENGTH: 65 amino acids
  (B) TYPE: amino acid
  (D) TOPOLOGY: linear (ii) MOLECULE TYPE: peptide (xi) SEQUENCE DESCRIPTION: SEQ ID NO:2:

```
Ala Thr Tyr Thr Asp Cys Thr Glu Ser Gly Gln Asn Leu Cys Leu Cys
 1               5                  10                  15

Glu Gly Ser Asn Val Cys Gly Gln Gly Asn Lys Cys Ile Leu Gly Ser
            20                  25                  30

Glu Gly Glu Lys Asn Gln Cys Val Thr Gly Glu Gly Thr Pro Lys Pro
            35                  40                  45

Gln Ser His Gln Glu Gly Glu Phe Glu Glu Ile Pro Glu Glu Tyr Leu
            50                  55                  60

Gln
65
```

(2) INFORMATION FOR SEQ ID NO:3:

(i) SEQUENCE CHARACTERISTICS:
  (A) LENGTH: 65 amino acids
  (B) TYPE: amino acid
  (D) TOPOLOGY: linear (ii) MOLECULE TYPE: peptide (ix) FEATURE:
  (A) NAME/KEY: Modified-site
  (B) LOCATION: 1
  (D) OTHER INFORMATION: /note="Xaa is any amino acid."

(ix) FEATURE:
  (A) NAME/KEY: Modified-site
  (B) LOCATION: 2
  (D) OTHER INFORMATION: /note="Xaa is any amino acid."

(ix) FEATURE:
  (A) NAME/KEY: Modified-site
  (B) LOCATION: 52
  (D) OTHER INFORMATION: /note="Xaa is Gln, Glu, Asn or Asp."

(ix) FEATURE:
  (A) NAME/KEY: Modified-site
  (B) LOCATION: 54
  (D) OTHER INFORMATION: /note="Xaa is Gly or Ala."

(ix) FEATURE:
  (A) NAME/KEY: Modified-site
  (B) LOCATION: 55
  (D) OTHER INFORMATION: /note="Xaa is Asp or Glu."

(xi) SEQUENCE DESCRIPTION: SEQ ID NO:3:

```
Xaa Xaa Tyr Thr Asp Cys Thr Glu Ser Gly Gln Asn Leu Cys Leu Cys
 1               5                  10                  15

Glu Gly Ser Asn Val Cys Gly Gln Gly Asn Lys Cys Ile Leu Gly Ser
            20                  25                  30

Glu Gly Glu Lys Asn Gln Cys Val Thr Gly Glu Gly Thr Pro Lys Pro
            35                  40                  45

Gln Ser His Xaa Glu Xaa Xaa Phe Glu Glu Ile Pro Glu Glu Tyr Leu
            50                  55                  60

Gln
```

65

(2) INFORMATION FOR SEQ ID NO:4:

(i) SEQUENCE CHARACTERISTICS:
        (A) LENGTH: 65 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note="Xaa is Leu, Ala, Ile or Val."

(ix) FEATURE:
        (A) NAME/KEY: Modified-site
        (B) LOCATION: 2
        (D) OTHER INFORMATION: /note="Xaa is Thr or Val."

(ix) FEATURE:
        (A) NAME/KEY: Modified-site
        (B) LOCATION: 33
        (D) OTHER INFORMATION: /note="Xaa is Glu."

(ix) FEATURE:
        (A) NAME/KEY: Modified-site
        (B) LOCATION: 52
        (D) OTHER INFORMATION: /note="Xaa is Gln or Glu."

(ix) FEATURE:
        (A) NAME/KEY: Modified-site
        (B) LOCATION: 54
        (D) OTHER INFORMATION: /note="Xaa is Gly or Ala."

(ix) FEATURE:
        (A) NAME/KEY: Modified-site
        (B) LOCATION: 55
        (D) OTHER INFORMATION: /note="Xaa is Asp or Glu."

(xi) SEQUENCE DESCRIPTION: SEQ ID NO:4:

```
Xaa  Xaa  Tyr  Thr  Asp  Cys  Thr  Glu  Ser  Gly  Gln  Asn  Leu  Cys  Leu  Cys
 1                    5                        10                        15

Glu  Gly  Ser  Asn  Val  Cys  Gly  Gln  Gly  Asn  Lys  Cys  Ile  Leu  Gly  Ser
               20                        25                        30

Xaa  Gly  Glu  Lys  Asn  Gln  Cys  Val  Thr  Gly  Glu  Gly  Thr  Pro  Lys  Pro
          35                        40                        45

Gln  Ser  His  Xaa  Glu  Xaa  Xaa  Phe  Glu  Glu  Ile  Pro  Glu  Glu  Tyr  Leu
     50                        55                        60

Gln
65
```

(2) INFORMATION FOR SEQ ID NO:5:

(i) SEQUENCE CHARACTERISTICS:
        (A) LENGTH: 65 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note="Xaa is Ala or Leu."

(xi) SEQUENCE DESCRIPTION: SEQ ID NO:5:

```
Xaa  Thr  Tyr  Thr  Asp  Cys  Thr  Glu  Ser  Gly  Gln  Asn  Leu  Cys  Leu  Cys
 1                    5                        10                        15
```

-continued

```
Glu Gly Ser Asn Val Cys Gly Gln Gly Asn Lys Cys Ile Leu Gly Ser
            20                  25                  30

Glu Gly Glu Lys Asn Gln Cys Val Thr Gly Glu Gly Thr Pro Lys Pro
            35                  40                  45

Gln Ser His Gln Glu Ala Asp Phe Glu Glu Ile Pro Glu Glu Tyr Leu
            50              55                  60

Gln
65
```

( 2 ) INFORMATION FOR SEQ ID NO:6:

( i ) SEQUENCE CHARACTERISTICS:
        ( A ) LENGTH: 65 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="Xaa is Ala or Leu."

( x i ) SEQUENCE DESCRIPTION: SEQ ID NO:6:

```
Xaa Thr Tyr Thr Asp Cys Thr Glu Ser Gly Gln Asn Leu Cys Leu Cys
1               5                   10                  15

Glu Gly Ser Asn Val Cys Gly Gln Gly Asn Lys Cys Ile Leu Gly Ser
            20                  25                  30

Glu Gly Glu Lys Asn Gln Cys Val Thr Gly Glu Gly Thr Pro Lys Pro
            35                  40                  45

Gln Ser His Gln Gln Gly Glu Phe Glu Glu Ile Pro Glu Glu Tyr Leu
            50              55                  60

Gln
65
```

( 2 ) INFORMATION FOR SEQ ID NO:7:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: Other
        ( A ) DESCRIPTION: synthetic DNA ( x i ) SEQUENCE DESCRIPTION: SEQ ID NO:7:

CCCGAAACCG CAGTCTCACC AGGAAGGCGA ATT        33

( 2 ) INFORMATION FOR SEQ ID NO:8:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: Other
        ( A ) DESCRIPTION: synthetic DNA ( x i ) SEQUENCE DESCRIPTION: SEQ ID NO:8:

CGAATTCGCC TTCCTGGTGA GACTGCGGTT TCGGGGTAC        39

( 2 ) INFORMATION FOR SEQ ID NO:9:

( i ) SEQUENCE CHARACTERISTICS:

( A ) LENGTH: 43 base pairs
( B ) TYPE: nucleic acid
( C ) STRANDEDNESS: single
( D ) TOPOLOGY: linear ( i i ) MOLECULE TYPE: Other
( A ) DESCRIPTION: synthetic DNA ( x i ) SEQUENCE DESCRIPTION: SEQ ID NO:9:

GATCCGAAGG TGAAAAGAAC CAGTGCGTTA CTGGCGAAGG TAC                    43

( 2 ) INFORMATION FOR SEQ ID NO:10:

( i ) SEQUENCE CHARACTERISTICS:
( A ) LENGTH: 35 base pairs
( B ) TYPE: nucleic acid
( C ) STRANDEDNESS: single
( D ) TOPOLOGY: linear ( i i ) MOLECULE TYPE: Other
( A ) DESCRIPTION: synthetic DNA ( x i ) SEQUENCE DESCRIPTION: SEQ ID NO:10:

CTTCGCCAGT AACGCACTGG TTCTTTTCAC CTTCG                              35

( 2 ) INFORMATION FOR SEQ ID NO:11:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( i i ) MOLECULE TYPE: Other
( A ) DESCRIPTION: synthetic DNA ( x i ) SEQUENCE DESCRIPTION: SEQ ID NO:11:

CCCGAAACCG CAGTCTCATA ACGAGGGCGA CTT                                33

( 2 ) INFORMATION FOR SEQ ID NO:12:

( i ) SEQUENCE CHARACTERISTICS:
( A ) LENGTH: 39 base pairs
( B ) TYPE: nucleic acid
( C ) STRANDEDNESS: single
( D ) TOPOLOGY: linear ( i i ) MOLECULE TYPE: Other
( A ) DESCRIPTION: synthetic DNA ( x i ) SEQUENCE DESCRIPTION: SEQ ID NO:12:

CGAAGTCGCC CTCGTTATGA GACTGCGGTT TCGGGGTAC                          39

( 2 ) INFORMATION FOR SEQ ID NO:13:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( i i ) MOLECULE TYPE: Other
( A ) DESCRIPTION: synthetic DNA ( x i ) SEQUENCE DESCRIPTION: SEQ ID NO:13:

CCCGAAACCG CAGTCTCATC AGGAGGCTGA CTT                                33

( 2 ) INFORMATION FOR SEQ ID NO:14:

( i ) SEQUENCE CHARACTERISTICS:
( A ) LENGTH: 39 base pairs
( B ) TYPE: nucleic acid (C) STRANDEDNESS: single
        (D) TOPOLOGY: linear (i i) MOLECULE TYPE: Other
        (A) DESCRIPTION: synthetic DNA (x i) SEQUENCE DESCRIPTION: SEQ ID NO:14:

CGAAGTCAGC CTCCTGATGA GACTGCGGTT TCGGGGTAC    39

(2) INFORMATION FOR SEQ ID NO:15:

(i) SEQUENCE CHARACTERISTICS:
        (A) LENGTH: 65 amino acids
        (B) TYPE: amino acid
        (D) TOPOLOGY: linear (i i) MOLECULE TYPE: peptide (i x) FEATURE:
        (A) NAME/KEY: Modified-site
        (B) LOCATION: 2
        (D) OTHER INFORMATION: /note="Xaa is Thr or Val."

(x i) SEQUENCE DESCRIPTION: SEQ ID NO:15:

Ala Xaa Tyr Thr Asp Cys Thr Glu Ser Gly Gln Asn Leu Cys Leu Cys
1               5                   10                  15

Glu Gly Ser Asn Val Cys Gly Gln Gly Asn Lys Cys Ile Leu Gly Ser
            20                  25                  30

Glu Gly Glu Lys Asn Gln Cys Val Thr Gly Glu Gly Thr Pro Lys Pro
        35                  40                  45

Gln Ser His Gln Glu Gly Glu Phe Glu Glu Ile Pro Glu Glu Tyr Leu
    50                  55                  60

Gln
65

(2) INFORMATION FOR SEQ ID NO:16:

(i) SEQUENCE CHARACTERISTICS:
        (A) LENGTH: 65 amino acids
        (B) TYPE: amino acid
        (D) TOPOLOGY: linear (i i) MOLECULE TYPE: peptide (i x) FEATURE:
        (A) NAME/KEY: Modified-site
        (B) LOCATION: 2
        (D) OTHER INFORMATION: /note="Xaa is Thr or Val."

(x i) SEQUENCE DESCRIPTION: SEQ ID NO:16:

Ala Xaa Tyr Thr Asp Cys Thr Glu Ser Gly Gln Asn Leu Cys Leu Cys
1               5                   10                  15

Glu Gly Ser Asn Val Cys Gly Gln Gly Asn Lys Cys Ile Leu Gly Ser
            20                  25                  30

Glu Gly Glu Lys Asn Gln Cys Val Thr Gly Glu Gly Thr Pro Lys Pro
        35                  40                  45

Gln Ser His Asn Glu Gly Asp Phe Glu Glu Ile Pro Glu Glu Tyr Leu
    50                  55                  60

Gln
65

(2) INFORMATION FOR SEQ ID NO:17:

(i) SEQUENCE CHARACTERISTICS:
        (A) LENGTH: 65 amino acids
        (B) TYPE: amino acid (D) TOPOLOGY: linear (i i) MOLECULE TYPE: peptide (i x) FEATURE:
  (A) NAME/KEY: Modified-site
  (B) LOCATION: 2
  (D) OTHER INFORMATION: /note="Xaa is Thr or Val."

(x i) SEQUENCE DESCRIPTION: SEQ ID NO:17:

| Ala | Xaa | Tyr | Thr | Asp | Cys | Thr | Glu | Ser | Gly | Gln | Asn | Leu | Cys | Leu | Cys |
|---|---|---|---|---|---|---|---|---|---|---|---|---|---|---|---|
| 1 | | | | 5 | | | | | 10 | | | | | 15 | |

| Glu | Gly | Ser | Asn | Val | Cys | Gly | Gln | Gly | Asn | Lys | Cys | Ile | Leu | Gly | Ser |
|---|---|---|---|---|---|---|---|---|---|---|---|---|---|---|---|
| | | | 20 | | | | | 25 | | | | | 30 | | |

| Glu | Gly | Glu | Lys | Asn | Gln | Cys | Val | Thr | Gly | Glu | Gly | Thr | Pro | Lys | Pro |
|---|---|---|---|---|---|---|---|---|---|---|---|---|---|---|---|
| | | 35 | | | | | 40 | | | | | 45 | | | |

| Gln | Ser | His | Gln | Glu | Ala | Asp | Phe | Glu | Glu | Ile | Pro | Glu | Glu | Tyr | Leu |
|---|---|---|---|---|---|---|---|---|---|---|---|---|---|---|---|
| | 50 | | | | | 55 | | | | | 60 | | | | |

Gln

65

(2) INFORMATION FOR SEQ ID NO:18:

(i) SEQUENCE CHARACTERISTICS:
    (A) LENGTH: 65 amino acids
    (B) TYPE: amino acid
    (D) TOPOLOGY: linear (i i) MOLECULE-TYPE: peptide (x i) SEQUENCE DESCRIPTION: SEQ ID NO:18:

| Ala | Thr | Tyr | Thr | Asp | Cys | Thr | Glu | Ser | Gly | Gln | Asn | Leu | Cys | Leu | Cys |
|---|---|---|---|---|---|---|---|---|---|---|---|---|---|---|---|
| 1 | | | | 5 | | | | | 10 | | | | | 15 | |

| Glu | Gly | Ser | Asn | Val | Cys | Gly | Gln | Gly | Asn | Lys | Cys | Ile | Leu | Gly | Ser |
|---|---|---|---|---|---|---|---|---|---|---|---|---|---|---|---|
| | | | 20 | | | | | 25 | | | | | 30 | | |

| Glu | Gly | Glu | Lys | Asn | Gln | Cys | Val | Thr | Gly | Glu | Gly | Thr | Pro | Lys | Pro |
|---|---|---|---|---|---|---|---|---|---|---|---|---|---|---|---|
| | | 35 | | | | | 40 | | | | | 45 | | | |

| Gln | Ser | His | Asn | Asp | Gly | Asp | Phe | Glu | Glu | Ile | Pro | Glu | Glu | Tyr | Leu |
|---|---|---|---|---|---|---|---|---|---|---|---|---|---|---|---|
| | 50 | | | | | 55 | | | | | 60 | | | | |

Gln

65

(2) INFORMATION FOR SEQ ID NO:19:

(i) SEQUENCE CHARACTERISTICS:
    (A) LENGTH: 65 amino acids
    (B) TYPE: amino acid
    (D) TOPOLOGY: linear (i i) MOLECULE TYPE: peptide (x i) SEQUENCE DESCRIPTION: SEQ ID NO:19:

| Ala | Thr | Tyr | Thr | Asp | Cys | Thr | Glu | Ser | Gly | Gln | Asn | Leu | Cys | Leu | Cys |
|---|---|---|---|---|---|---|---|---|---|---|---|---|---|---|---|
| 1 | | | | 5 | | | | | 10 | | | | | 15 | |

| Glu | Gly | Ser | Asn | Val | Cys | Gly | Gln | Gly | Asn | Lys | Cys | Ile | Leu | Gly | Ser |
|---|---|---|---|---|---|---|---|---|---|---|---|---|---|---|---|
| | | | 20 | | | | | 25 | | | | | 30 | | |

| Asp | Gly | Glu | Lys | Asn | Gln | Cys | Val | Thr | Gly | Glu | Gly | Thr | Pro | Lys | Pro |
|---|---|---|---|---|---|---|---|---|---|---|---|---|---|---|---|
| | | 35 | | | | | 40 | | | | | 45 | | | |

| Gln | Ser | His | Gln | Glu | Gly | Glu | Phe | Glu | Glu | Ile | Pro | Glu | Glu | Tyr | Leu |
|---|---|---|---|---|---|---|---|---|---|---|---|---|---|---|---|
| | 50 | | | | | 55 | | | | | 60 | | | | |

Gln

65

( 2 ) INFORMATION FOR SEQ ID NO:20:

( i ) SEQUENCE CHARACTERISTICS:
        ( A ) LENGTH: 65 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:20:

```
Ala Thr Tyr Thr Asp Cys Thr Glu Ser Gly Gln Asn Leu Cys Leu Cys
 1               5                  10                      15

Glu Gly Ser Asn Val Cys Gly Gln Gly Asn Lys Cys Ile Leu Gly Ser
             20                  25                  30

Asp Gly Glu Lys Asn Gln Cys Val Thr Gly Glu Gly Thr Pro Lys Pro
         35                  40                  45

Gln Ser His Asn Asp Ala Asp Phe Glu Glu Ile Pro Glu Glu Tyr Leu
     50                  55                      60

Gln
 65
```

( 2 ) INFORMATION FOR SEQ ID NO:21:

( i ) SEQUENCE CHARACTERISTICS:
        ( A ) LENGTH: 65 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:21:

```
Ala Thr Tyr Thr Asp Cys Thr Glu Ser Gly Gln Asn Leu Cys Leu Cys
 1               5                  10                      15

Glu Gly Ser Asn Val Cys Gly Gln Gly Asn Lys Cys Ile Leu Gly Ser
             20                  25                  30

Glu Gly Glu Lys Asn Gln Cys Val Thr Gly Glu Gly Thr Pro Lys Pro
         35                  40                  45

Gln Ser His Asn Asp Ala Asp Phe Glu Glu Ile Pro Glu Glu Tyr Leu
     50                  55                      60

Gln
 65
```

( 2 ) INFORMATION FOR SEQ ID NO:22:

( i ) SEQUENCE CHARACTERISTICS:
        ( A ) LENGTH: 65 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:22:

```
Ala Thr Tyr Thr Asp Cys Thr Glu Ser Gly Gln Asn Leu Cys Leu Cys
 1               5                  10                      15

Glu Gly Ser Asn Val Cys Gly Gln Gly Asn Lys Cys Ile Leu Gly Ser
             20                  25                  30

Asp Gly Glu Lys Asn Gln Cys Val Thr Gly Glu Gly Thr Pro Lys Pro
         35                  40                  45

Gln Ser His Asn Glu Gly Asp Phe Glu Glu Ile Pro Glu Glu Tyr Leu
     50                  55                      60

Gln
```

65

(2) INFORMATION FOR SEQ ID NO:23:

(i) SEQUENCE CHARACTERISTICS:
        (A) LENGTH: 65 amino acids
        (B) TYPE: amino acid
        (D) TOPOLOGY: linear (ii) MOLECULE TYPE: peptide (xi) SEQUENCE DESCRIPTION: SEQ ID NO:23:

```
Ala Thr Tyr Thr Asp Cys Thr Glu Ser Gly Gln Asn Leu Cys Leu Cys
 1               5                  10                  15

Glu Gly Ser Asn Val Cys Gly Gln Gly Asn Lys Cys Ile Leu Gly Ser
             20                  25                  30

Asp Gly Glu Lys Asn Gln Cys Val Thr Gly Glu Gly Thr Pro Lys Pro
             35                  40                  45

Gln Ser His Asn Glu Gly Asp Phe Glu Glu Ile Pro Glu Glu Tyr Leu
             50                  55                  60

Gln
 65
```

(2) INFORMATION FOR SEQ ID NO:24:

(i) SEQUENCE CHARACTERISTICS:
        (A) LENGTH: 65 amino acids
        (B) TYPE: amino acid
        (D) TOPOLOGY: linear (ii) MOLECULE TYPE: peptide (xi) SEQUENCE DESCRIPTION: SEQ ID NO:24:

```
Ala Thr Tyr Thr Asp Cys Thr Glu Ser Gly Gln Asn Leu Cys Leu Cys
 1               5                  10                  15

Glu Gly Ser Asn Val Cys Gly Gln Gly Asn Lys Cys Ile Leu Gly Ser
             20                  25                  30

Asp Gly Glu Lys Asn Gln Cys Val Thr Gly Glu Gly Thr Pro Lys Pro
             35                  40                  45

Gln Ser His Gln Glu Ala Asp Phe Glu Glu Ile Pro Glu Glu Tyr Leu
             50                  55                  60

Gln
 65
```

(2) INFORMATION FOR SEQ ID NO:25:

(i) SEQUENCE CHARACTERISTICS:
        (A) LENGTH: 65 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note="Xaa is Ala or Leu."

(xi) SEQUENCE DESCRIPTION: SEQ ID NO:25:

```
Xaa Thr Tyr Thr Asp Cys Thr Glu Ser Gly Gln Asn Leu Cys Leu Cys
 1               5                  10                  15

Glu Gly Ser Asn Val Cys Gly Gln Gly Asn Lys Cys Ile Leu Gly Ser
             20                  25                  30
```

```
            Glu  Gly  Glu  Lys  Asn  Gln  Cys  Val  Thr  Gly  Glu  Gly  Thr  Pro  Lys  Pro
                      35                      40                      45

Gln  Ser  His  Gln  Glu  Gly  Glu  Phe  Glu  Glu  Ile  Pro  Glu  Glu  Tyr  Leu
                 50                      55                      60

Gln
            65
```

( 2 ) INFORMATION FOR SEQ ID NO:26:

( i ) SEQUENCE CHARACTERISTICS:
        ( A ) LENGTH: 65 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="Xaa is Ala or Leu."

( x i ) SEQUENCE DESCRIPTION: SEQ ID NO:26:

```
            Xaa  Thr  Tyr  Thr  Asp  Cys  Thr  Glu  Ser  Gly  Gln  Asn  Leu  Cys  Leu  Cys
            1                       5                       10                      15

Glu  Gly  Ser  Asn  Val  Cys  Gly  Gln  Gly  Asn  Lys  Cys  Ile  Leu  Gly  Ser
                      20                      25                      30

Glu  Gly  Glu  Lys  Asn  Gln  Cys  Val  Thr  Gly  Glu  Gly  Thr  Pro  Lys  Pro
                      35                      40                      45

Gln  Ser  His  Gln  Glu  Gly  Glu  Phe  Glu  Glu  Ile  Pro  Glu  Glu  Tyr  Leu
                 50                      55                      60

Gln
            65
```

( 2 ) INFORMATION FOR SEQ ID NO:27:

( i ) SEQUENCE CHARACTERISTICS:
        ( A ) LENGTH: 65 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="Xaa is Ala or Leu."

( i x ) FEATURE:
        ( A ) NAME/KEY: Modified-site
        ( B ) LOCATION: 2
        ( D ) OTHER INFORMATION: /note="Xaa is Thr or Val."

( x i ) SEQUENCE DESCRIPTION: SEQ ID NO:27:

```
            Xaa  Xaa  Tyr  Thr  Asp  Cys  Thr  Glu  Ser  Gly  Gln  Asn  Leu  Cys  Leu  Cys
            1                       5                       10                      15

Glu  Gly  Ser  Asn  Val  Cys  Gly  Gln  Gly  Asn  Lys  Cys  Ile  Leu  Gly  Ser
                      20                      25                      30

Glu  Gly  Glu  Lys  Asn  Gln  Cys  Val  Thr  Gly  Glu  Gly  Thr  Pro  Lys  Pro
                      35                      40                      45

Gln  Ser  His  Gln  Glu  Ala  Asp  Phe  Glu  Glu  Ile  Pro  Glu  Glu  Tyr  Leu
                 50                      55                      60

Gln
            65
```